United States Patent
Tomsia et al.

(10) Patent No.: US 8,012,590 B2
(45) Date of Patent: Sep. 6, 2011

(54) GLASS/CERAMIC COATINGS FOR IMPLANTS

(75) Inventors: Antoni P. Tomsia, Pinole, CA (US); Eduardo Saiz, Berkeley, CA (US); Jose M. Gomez-Vega, Nagoya (JP); Sally J. Marshall, Larkspur, CA (US); Grayson W. Marshall, Larkspur, CA (US)

(73) Assignee: The Regents of the University of California, Oakland, CA (US)

( * ) Notice: Subject to any disclaimer, the term of this patent is extended or adjusted under 35 U.S.C. 154(b) by 133 days.

(21) Appl. No.: 09/845,597

(22) Filed: Apr. 30, 2001

(65) Prior Publication Data

US 2002/0076528 A1    Jun. 20, 2002

Related U.S. Application Data

(60) Provisional application No. 60/201,556, filed on May 1, 2000.

(51) Int. Cl.
  *B32B 17/05* (2006.01)
  *B32B 27/38* (2006.01)
  *B32B 27/40* (2006.01)

(52) U.S. Cl. ........ 428/426; 428/414; 428/415; 428/416; 428/425.6; 428/432

(58) Field of Classification Search ................. 428/426, 428/432, 433, 689, 697, 699, 701, 702; 501/55, 501/63, 69, 72, 32; 106/35
  See application file for complete search history.

(56) References Cited

U.S. PATENT DOCUMENTS

| | | | |
|---|---|---|---|
| 4,842,653 A | | 6/1989 | Wirth et al. |
| 5,068,122 A | * | 11/1991 | Kokubo et al. ........... 427/2.1 |
| 5,077,132 A | * | 12/1991 | Maruno et al. ........... 428/426 |
| 5,125,971 A | | 6/1992 | Nonami et al. |
| 5,232,878 A | * | 8/1993 | Kasuga et al. ........... 501/10 |
| 5,478,237 A | | 12/1995 | Ishizawa |
| 5,562,733 A | * | 10/1996 | Weissbach et al. ........... 623/16 |
| 5,648,302 A | | 7/1997 | Brow et al. |
| 5,665,121 A | * | 9/1997 | Gie et al. ........... 623/16 |
| 5,849,649 A | | 12/1998 | Poole |
| 6,045,914 A | | 4/2000 | Sullivan et al. |
| 6,069,295 A | | 5/2000 | Leitao |
| 6,113,993 A | | 9/2000 | Gao et al. |

(Continued)

OTHER PUBLICATIONS

J.M. Gomez-Vega, E. Saiz, A.P. Tomsia, G.W. Marshall, and S.J. Marshall, "A multilayer approach to fabricate bioactive glass coatings on Ti alloys" (Dec. 1, 1998). Lawrence Berkeley National Laboratory. Paper LBNL-46553. http://repositories.cdlib.org/lbnl/LBNL-46553.*

(Continued)

*Primary Examiner* — Donald L. Tarazano
*Assistant Examiner* — Camie Thompson
(74) *Attorney, Agent, or Firm* — Robin C. Chiang; Lawrence Berkeley National Laboratory

(57) ABSTRACT

Glass coatings on metals including Ti, Ti6A14V and CrCo were prepared for use as implants. The composition of the glasses was tailored to match the thermal expansion of the substrate metal. By controlling the firing atmosphere, time, and temperature, it was possible to control the reactivity between the glass and the alloy and to fabricate coatings (25-150 μm thick) with excellent adhesion to the substrate. The optimum firing temperatures ranged between 800 and 840° C. at times up to 1 min in air or 15 min in $N_2$. The same basic technique was used to create multilayered coatings with concentration gradients of hydroxyapatite (HA) particles and $SiO_2$.

17 Claims, 5 Drawing Sheets

Multilayers of Glass/HA

U.S. PATENT DOCUMENTS 6,146,686 A     11/2000   Leitao
6,207,218 B1     3/2001   Layrolle et al.

OTHER PUBLICATIONS

J.M. Gomez-Vega, E. Saiz, A.P. Tomsia, G.W. Marshall, and S.J. Marshall, "A multilayer approach to fabricate bioactive glass coatings on Ti alloys", Presented on Dec. 1, 1998 at the MRS 1998 Fall Meeting in Boston, MA.*

Gomez-Vega, et al. "Novel Bioactive Functionally Graded Coatings on Ti6Al4V", (Mar. 1, 2000), http://www.osti.gov/energycitations/product.biblio.jsp?osti_id=767586.*

Gomez-Vega, J.M., Saiz, E., Tomsia, A.P., Marshall, G.W., & Marshall, S.J.(1998). A multilayer approach to fabricate bioactive glass coatings on Ti alloys. Lawrence Berkeley National Laboratory: Lawrence Berkeley National Laboratory. LBNL Paper LBNL-46553. Retrieved from: http://escholarship.org/uc/item/1mh5w6zr.*

Gomez-Vega, J.M., Saiz, E., Tomsia, A.P., Marshall, G.W., & Marshall, S.J.(1998). A multilayer approach to fabricate bioactive glass coatings on Ti alloys. Conference, MRS Fall Meeting 1998. Retrieved from: http://www.osti.gov/energycitations/product.biblio.jsp?query_id=1&page=0&osti_id=788020.*

A.P. Tomsia et al, "New route for Hydroxyapatite coatings on Ti-based human implants," Scipta Met. Et Mat., vol. 31 ( No. 8), p. 995-1000, (1994).

J.S. Moya et al, "In vitro formation of Hydroxylapatite layer in a MgO-containing glass," J. Mat. Sci. Mat. in Med., vol. 5 ( No. 8), p. 529-532, (1994).

A Pazo, et al, "HA-Bioactive glass composites—high temperature reactivity and in vitro behavior," Scripta Materialia, vol. 34 ( No. 11), p. 1729-1733, (1996).

A. Pazo et al., "Bioactive coatings on Ti and Ti6Al4V alloys for medical applications," Ceramic Microstructures: Control at the Atomic Level, Plenum P. (New York), p. 543-550, (1998).

A. Pazo et al, "Silicate glass coatings on Ti-based implants," Acta Mater., vol. 46 ( No. 7), p. 2551-2558, (1998).

E. Salz et al., "Bioactive Glass Catings on Ti-based Implants," Trans. 24th Annual Meeeting Society for Biomaterials, p. 243, (1998).

M. Gomez-Vega et al., "Glass-based coatings for titanium implant alloys," J. Biomet.Mater. Res., p. 549-559, (1999).

M. Gomez-Vega et al., "A multilayer approach to fabricate bioactive glass coatings on Ti alloys," Biomedical Materials: Drug Delivery, Implants and Tissue Engineering, Mater. Res. Soc. Symp. Proc., p. 349-354, (1999).

D.R. Bloyer et al., "Subcritical crack growth of bioactive glasses in simulated body fluid," Biomedical Materials: Drug Delivery, Implants and Tissue Engineering, Mater. Res. Soc. Symp. Proc., p. 355-359, (1999).

J.M. Gomez-Vega et al., "Fabrication and characterization of a bioactive glass coating on titanium implant alloys." Acta Mater., vol. 47 ( No. 15-), p. 4221-4224, (1999).

J.M. Gomez-Vega et al., "Bioactive glass coatings with hydrosyapatite and Bioglass particles on Ti-based implants. I. Processing," Biomaterials, vol. 21 ( No. 2), p. 105-111, (2000).

J.M. Gomez-Vega, "Glass-Hydroxyapatite coatings on titanium-based implants," Ceramic Transactions, accepted for publication, Dec. 1999.

J.M. Gomez-Vega et al, "Novel bioactive functionally graded coatings on Ti6Al4V," Trans. 6th World Congress for Society for Biomaterials, accepted for publication in Adv. Mater, Jun. 2000.

A. Pazo et al, "Glass coatings on Ti implant alloys," J. Dent. Res., vol. 76 ( No. SI), p. 1513, (1997).

A.P. Tomsia et al., "Graded bioactive coatings on Ti implants," Am. Ceram. Soc. Bull., vol. 77 ( No. 4), p. 191, (1998).

D.R. Bloyer et al., "Environmentally assisted crack growth in novel bioactive glasses," Am. Ceram. Soc. Bull., vol. 77 (No. 4), p. 190, (1998).

J.M. Gomez-Vega et al., "Layered glass coatings on Ti implants," J. Dent. Res., vol. 77 ( No. SI), p. A-17, (1998).

D.R. Bloyer et al., "Stress Corrosion Crack Growth in Bioactive Glass," J. Dent. Res., vol. 78 ( No. SI), p. 177, (1999).

J.M. Gomez-Vega et al., "Graded Bioactive Glass Coatings on Ti6Al4V," J. Dent. Res., vol. 78 ( No. SI), p. 178, (1999).

* cited by examiner

GLASS/CERAMIC COATINGS FOR IMPLANTS

CROSS REFERENCE TO RELATED APPLICATIONS

This application claims priority from the following application: U.S. Application No. 60/201,556 filed May 1, 2000.

STATEMENT REGARDING FEDERALLY SPONSORED RESEARCH OR DEVELOPMENT

This invention was made with government support under Grant (Contract) No. DE-AC03-76F00098 awarded by The United States Department of Energy. The United States Government has certain rights to this invention.

BACKGROUND OF THE INVENTION

Titanium and Ti6Al4V alloy are widely used as materials for orthopedic implants because of their advantageous mechanical properties and nontoxic behavior, Benjamin, D., editor. Metals handbook, Volume 3, 9th ed., Metals Park, Ohio: American Society for Metals; 1980, p 372-406; and Dobbs, H. S., *Fracture of titanium orthopedic implants.*, J. Mater. Sci., 1982; 17: 2398-2340. However, one of the main drawbacks of using metallic implants is that they are bioinert and become encapsulated by dense fibrous tissue inside the body. This impedes proper stress distribution at the implant-bone interface, which can result in an interfacial failure and loosening of the implant with the possible consequence of fracture in the adjacent bone, Hench, L. L., *Bioceramics: from concept to clinic*, J. Am. Ceram. Soc., 1991; 74:1487-1510; and Suchanek, W. et al., *Processing and properties of hydroxyapatite-based biomaterials for use as hard tissue replacement implants*, Mater. Res., 1998, 13; 94-117.

In addition, the use of polymethylmethacrylate bone cement to improve implant fixation can result in the deterioration of the adjacent bone. There have been approximately 40 deaths in Japan allegedly associated to bone cements, "Bone Cement Kills 37 since 1987", Pharmaceuticals and Medical Devices Safety Information No. 165, Mar. 30 (2001), Ministry of Health Labour and Welfare, Japan. A way to solve this problem and to improve the performance of metallic implants is to coat them with a bioactive material. A bioactive coating with good adhesion to the metal can also bond interfacially to the bone, which will accelerate the stabilization of the implant and extend its duration. Synthetic hydroxyapatite (HA) is very similar to the inorganic component of bone and it has proven to be bioactive, LeGeros, R. Z. et al., *Dense hydroxyapatite* In: Hench, L. L. et al., Editors: An introduction to bioceramics, Singapore: World Scientific; 1993 pp. 139-180; and Shors, E. C. et al., *Porous hydroxyapatite*: In: Hench, L. L. et al., Editors: An introduction to bioceramics, Singapore: World Scientific; 1993 pp. 181-198. Consequently, during recent years several groups investigated the fabrication of HA coatings on metallic implants; plasma-spray coating was the preferred technique, Lacefield, W. R., *Hydroxylapatite coating* In: Hench, L. L. et al., Editors: An introduction to bioceramics, Singapore: World Scientific; 1993 pp. 223-238; and Ha, S. W. et al., *Chemical and morphological changes of vacuum-plasma-sprayed hydroxyapatite coatings during immersion in simulated physiological solutions*, J. Am. Ceram. Soc. 1998; 81:81-88.

Reports about the performance of plasma-sprayed coatings seem to indicate that there is a faster adaptation of the bone to the implant and an appreciable improvement of the interfacial strength at the early stages. However, there is still some lack of data about the long-term efficiency of the plasma-sprayed coatings. Usually, the plasma-sprayed coatings consist of a mixture of amorphous and crystalline phases. The fast dissolution of the amorphous phase and some of the crystalline products like tricalcium phosphate degrade the stability of the coating. Further heat treatment to improve the crystallinity often results in cracking and loss of adhesion. Finally, plasma spray is a "line of sight" technique, which is not entirely suitable for coating implants that have complex shapes.

An alternative method is to coat the implant with a bioactive glass (able to form HA in vivo) that could provide the desired interfacial attachment to the bone. Several groups have attempted to coat metallic implants with bioactive glasses using enameling, rapid immersion in molten glass, or plasma-spraying techniques. Although some coatings with excellent in-vitro behavior were obtained, most of the glass coatings were marred by cracking and poor reliability at the glass-metal interface, Hench, L. L. et al., *Bioactive glass coatings*, In: Hench, L. L. et al., Editors, An introduction to bioceramics, Singapore: World Scientific; 1993 pp. 239-260; and Lee, T. M. et al., *Characteristics of plasma-sprayed bioactive glass coatings on Ti6Al4V alloy: an in vitro study*, Surface Coatings Technol. 1996, 79:170-177; and Kitsugi, T. et al., *Bone-bonding behavior of plasma-sprayed coatings of Bioglass™, AW-glass ceramic, and tricalcium phosphate on titanium alloy*. J. Biomed. Mater. Res. 1996, 30: pp. 261-260; and Chern, L. et al., *Corrosion behavior of hydroxyapatite/bioactive glass plasma sprayed on $Ti_6Al_4V$*, Mater. Chem. Phys. 1995 41: pp. 282-289. In particular, when coating Ti and Ti alloys, space problems result primarily from the generation of high thermal stresses, which arise from the difference in thermal expansion between the glass and the metal and the high reactivity of Ti with $SiO_2$-based glasses. The reactions lead to the formation of brittle interfacial layers and gas bubbles in the coating.

Previous studies showed that it is possible to obtain bioactive glasses in the $SiO_2$—CaO—MgO—$Na_2O$—$K_2O$—$P_2O_5$ system and glasses able to form HA in vitro with $SiO_2$, contents as high as 57 wt %. These glasses present adequate softening points and thermal expansions close to Ti6Al4V ($\alpha_{Ti6Al4V} \approx 9.1$-$9.8 \times 10^{-6}$ $C.^{-1}$ at 400° C.), Pazo, A. et al., *HA-bioactive glass composites: high temperature reactivity and "in vitro" behavior*, Scripta. Mater. 1996 34:pp. 1729-1733; and Pazo, A. et al., *Silicate glass coatings on Ti-based implants*, Acta. Mater. 1998: 46:pp. 2551-2558. Thus, they are candidates for use as coatings per se or mixed with other crystalline phases like HA as homogeneous or layered composites.

BRIEF SUMMARY OF THE INVENTION

The aim of the present work was to develop bioactive glass coatings on metal, in particular Ti, Ti6Al4V and CoCr alloys. The composition of the glass is tailored to match the thermal expansion of the metal or metal alloy. Glasses of the general composition $SiO_2$—CaO—MgO—$Na_2O$—$K_2O$—$P_2O_5$ are used, and hydroxyapatite (HA) particles are added to the composition. The fabrication of coatings where the Si content and HA content is a gradient, preferably in a direction perpendicular to the substrate surface, are contemplated by this invention.

Multilayered articles are proposed. Gradients in compositions in the layers are proposed which result in a gradient in thermal expansion, that will increase the mechanical stability of coatings whose external layer will have a lower $SiO_2$ content than the internal layer. In general, it is possible to fabricate coatings with an outer layer having a silica content as low as 53% that did not crack and/or delaminate during cooling or indentation.

A coating with a concentration gradient of $SiO_2$, with low silica content (higher bioactivity) in/on the outer layer is contemplated by this invention. Further, a coating with a concentration gradient of HA, having a higher HA content in the outer layer resulting in a glass/HA ratio that decreases closer towards the bioactive surface (more HA towards the bioactive surface).

The multilayered article coating is preferably accomplished by depositing different layers having different concentrations of materials, but it is also contemplated that the gradient may be accomplished by other means not relying on deposition techniques.

Single layers with a gradient of HA are also contemplated by the instant invention.

In the instant invention, the softening point of the glass is tailored to be low enough to keep the firing temperature below the $\alpha \to \beta$ transformation of Ti (955-1010° C. in Ti6Al4V). A very effective way of decreasing the thermal expansion coefficient of the glass and approach the one of Ti6Al4V is to increase its silica content. The selected glass powders were deposited on the metal substrate and fired in order to make the glass flow and adhere. The firing was done in air in order to preoxidize the alloy as in a conventional enameling process or in nitrogen in order to form an interfacial (Ti nitride) layer that could buffer interfacial reactions and provide good adhesion.

DETAILED DESCRIPTION OF THE PREFERRED EMBODIMENTS

Figure 1:
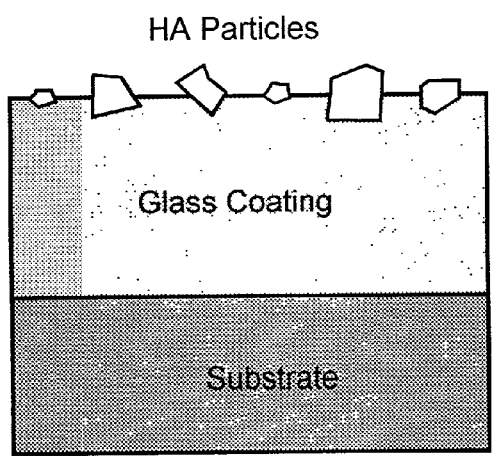
FIG. 1 demonstrates a dual layered structure with HA particles protruding from the surface of the glass coating.

The instant invention contemplates glass compositions that can be used to prepare glass coatings on metal alloys, particularly Ti, Ti6Al4V and CrCo alloys. The composition of the glass is preferably formulated to obtain thermal expansion close to the metal or alloy and the appropriate softening point to make the glass flow and adhere at temperatures below the $\alpha \to \beta$ transformation of Ti. Glasses with $SiO_2$ contents between 56 and 68 wt % are preferred for Ti and Ti6Al4V. For CoCr alloys glasses with a lower silica content, 50-56 wt % are preferable.

During firing of the coatings in air or $N_2$ an oxide or nitride layer develops on the surface of the substrate. By controlling the firing time and temperature it is possible to make the glass flow and form a dense layer and then stop the process after it dissolves the oxide or nitride but before the glass reacts extensively with the substrate. This invention contemplates an optimum firing temperature and through numerous investigations and studies the investigators have found that the firing temperature increases with increased $SiO_2$ content. The preferred firing temperature ranges between 800 and 840° C. for up to 1 min in air and 15 min in $N_2$. For CrCo the preferred firings occur at lower temperatures and longer times.

The invention described herein contemplates an implant comprising a layered structure. The implant may be any implant used by the medical profession, including teeth. The multilayered coating proposed herein results in increased performance of the implant. The increased performance included improved bone to implant bonding, integrity, adhesion and the ability to design coatings with an internal insoluble glass layer that can protect the metallic implant from corrosion, while maintaining a bioactive surface. By using a multilayered approach it is possible to fabricate coatings with low silica content on the outside, and a higher concentration of hydroxyapatite on the outside, which means a higher bioactivity on the outer surface.

All percentages are expressed in weight percent unless otherwise specified. When the invention described herein states "about", it is contemplated that the values given are valid +/−0.1 wt %. Weight percentages of the glass composition alone is based on the total weight of the glass system encompassing $SiO_2$—CaO—MgO—$Na_2O$—$K_2O$—$P_2O_5$. Weight percentages for the glass/HA admixture are based on the total admixture, glass and HA.

Ti6Al4V herein refers to a standard alloy composition. The numbers refer to a weight % of its contents.

A glass/hydroxyapatite admixture refers to a mixture of a glass composition and hydroxyapatite particles. The glass composition may comprise a mixture of two or more glasses.

A glass composition refers to a mixture of oxides comprising about 44.2 to about 67.7 wt % $SiO_2$, about 10.1 to about 23.4 wt % CaO, about 5.7 to about 13.3 wt % MgO, about 8.3 to about 23.6 wt % $Na_2O$, about 2.2 to about 6.5 wt % $K_2O$ and about 6.0 wt % $P_2O_5$. Preferably the glass composition is one of the compositions set forth in Table 1.

Substrate as referred to herein refers to a metal or metal alloy. Preferred are Ti, Ti6Al4V and CrCo alloys. "Coating" as referred to herein implies the standard meaning and also means a single layer or a combination of a multitude of layers.

As used herein, inner layers or surfaces refer to layers nearer the substrate, and outer layers or outer surfaces refer to layers or surfaces located away from the substrate, relative to inner layers. Thus, an inner layer would be closer the substrate than an outer layer. There may be many inner and outer layers; for example it is contemplated that there may be 3 inner layers, and an outer layer. Alternatively, there may be 1 inner layer and 3 outer layers, all 3 outer layers are then further away from the substrate than the single inner layer. Where the layers are referred to as "n" it is to be understood that in a multilayered structure, the value of n increases towards the substrate. Thus if n=3, the multilayered structure would be substrate/n=3 intermediate layer/n=2 intermediate layer/n=1 intermediate layer/first layer. The instant invention contemplates no particular number of intermediate layers. The value of "n" is chosen depending on the desired end use. Preferably n is small, on the order of 2 or 3.

The thicknesses of the layers is readily determinable by one having ordinary skill in the art depending on the desired end use. Thicknesses of the layers in the range of 25-200 μm are preferred, with a thickness in the 10-30 μm being more preferred. Generally, it is preferred to have a thinner layer on the outside.

As referred to herein, "gradient concentration" or "concentration gradient" means the concentration varies from a higher value to a lower value, or vice versa. The The term "gradient" is not intended to suggest that the concentration varies uniformly. Although this may be the case with respect to some layers, it is not a requirement.

The hydroxyapatite (HA) particles used in the instant invention have particle sizes ranging from the nm size up to 150 μm. Preferred is approximately 1-20 μm and more preferably about 1-5 μm. When the particles get too small the glass dissolves the particles.

A number of calcium phosphate minerals, such as fluorapatite, octacalcium phosphate (OCaP), whitlockite (Beta-TCP), TCP, brushite and monetite are known in the art as biocompatible minerals. Thus, this inventions contemplates that these and other biocompatable materials may be substituted for hydroxyapatite and are suitable for use in the invention contemplated herein. These are also referred to as ceramics.

Glasses in the $SiO_2$—$CaO$—$MgO$—$Na_2O$—$K_2O$—$P_2O_5$ system were prepared by mixing the reagents in ethanol using a high-speed stirrer. The $P_2O_5$ content was fixed at 6 wt % for all the glasses, so they are named 6P followed by their SiO, content in weight percent (Table 1).

TABLE 1

Glass Compositions

| | $SiO_2$ | $Na_2O$ | $K_2O$ | CaO | MgO | $P_2O_5$ |
|---|---|---|---|---|---|---|
| Bioglass ® | 45.0 | 24.5 | | 24.5 | | 6.0 |
| 6P44-a | 44.2 | 23.6 | 6.5 | 12.6 | 7.1 | 6.0 |
| 6P44-b | 44.2 | 17.0 | 4.6 | 18.0 | 10.2 | 6.0 |
| 6P44-c | 44.2 | 10.3 | 2.8 | 23.4 | 13.3 | 6.0 |
| 6P50 | 49.8 | 15.5 | 4.2 | 15.6 | 8.9 | 6.0 |
| 6P53-a | 52.7 | 17.0 | 4.6 | 12.6 | 7.1 | 6.0 |
| 6P53-b | 52.7 | 10.3 | 2.8 | 18.0 | 10.2 | 6.0 |
| 6P55 | 54.5 | 12.0 | 4.0 | 15.0 | 8.5 | 6.0 |
| 6P57 | 56.5 | 11.0 | 3.0 | 15.0 | 8.5 | 6.0 |
| 6P61 | 61.1 | 10.3 | 2.8 | 12.6 | 7.2 | 6.0 |
| 6P68 | 67.7 | 8.3 | 2.2 | 10.1 | 5.7 | 6.0 |

The reagents were $SiO_2$, (99.5%, Cerac), $CaCO_3$, (99.9%, J. T. Baker), MgO (98.6%, J. T. Baker), $K_2CO_3$, (99%, Allied Chemical), $NaHCO_3$ (99.5%, J. T. Baker), and $NaPO_3$ (99.7%, Allied Chemical). The mixture was first dried at 80° C. for 12 h and then fired in air at 1400° C. for 4 h in a Pt crucible (with the exception of 6P68, which was fired at 1500° C. because of its high $SiO_2$ content). The melt was cast into a graphite mold to obtain glass plates (approx. 50×50×5 mm) that were subsequently annealed at 500° C. for 6 h to relieve stresses. The thermal expansion ($\alpha$), softening ($T_s$), and transformation ($T_g$) temperatures were measured in a calibrated dilatometer with an alumina holder and push rod and using 25-mm length glass bars. To manufacture the coatings, the glass was milled in a planetary agate mill and a suspension of the glass powder (particle size <20 μm) in ethanol was deposited on Ti6Al4V plates (99.0% purity, 15×10×1 mm), which had been previously polished with diamond (1 and 6 μm particle size) and cleaned in acetone and ethanol. Afterward, the coatings were dried in air at 75° C. overnight.

Multilayered coatings were manufactured by depositing two or three (or more) different glass layers on the metal substrates using the previously described method. Layered glass coatings with embedded HA particles (<20 μm) were also fabricated; in these coatings the outermost layer was a composite of glass and HA (50:50 wt %). In this way, it was possible to prepare multi- or monolayer coatings with controlled thicknesses ranging between 25 and 150 μm. One embodiment of the instant invention contemplates a multilayer article comprising, a metal substrate, n intermediate layers, where n is an integer, a first layer comprising an inner and outer surface, said n intermediate layers disposed between the metal substrate and the first layer, wherein the n intermediate layers and the first layer each independently comprise a glass/hydroxyapatite admixture comprising a glass composition and hydroxyapatite particles (HA), said glass composition comprising, about 44.2 to about 67.7 wt % $SiO_2$, about 10.1 to about 23.4 wt % CaO, about 5.7 to about 13.3 wt % MgO, about 8.3 to about 23.6 wt % $Na_2O$, about 2.2 to about 6.5 wt % $K_2O$ and about 6.0 wt % $P_2O_5$, and wherein said hydroxyapatite particles being present in the glass/hydroxyapatite admixture in an amount of 0.0 wt % to about 50 wt %, such that the first layer has a hydroxyapatite concentration greater than all layers under it, each n intermediate layer under the first layer has a hydroxyapatite concentration greater than the n intermediate layer under it, so there is a gradient of glass/hydroxyapatite admixtures in the multilayered article such that the highest concentration of hydroxyapatite is found in the first layer and the least is found in the n intermediate layer next to the substrate, and the glass composition for each layer is chosen such that there such that the first layer has a $SiO_2$ concentration less than all layers under it, and each n intermediate layer under the first layer has a $SiO_2$ concentration less than the n intermediate layer under it, so there is a gradient of $SiO_2$ concentration in the admixtures in the multilayered article such that the highest concentration of $SiO_2$ is found in the n intermediate layer next to the substrate and the least is found in the first layer.

Another embodiment of the invention contemplates a multilayer article comprising, a metal substrate, n intermediate layers, where n is an integer, a first layer comprising an inner and outer surface, said n intermediate layers disposed between the metal substrate and the first layer, wherein the n intermediate layers and the first layer each independently comprise a glass/hydroxyapatite admixture comprising a glass composition and hydroxyapatite particles (HA), said glass composition comprising, about 44.2 to about 67.7 wt % $SiO_2$, about 10.1 to about 23.4 wt % CaO, about 5.7 to about 13.3 wt % MgO, about 8.3 to about 23.6 wt % $Na_2O$, about 2.2 to about 6.5 wt % $K_2O$ and about 6.0 wt % $P_2O_5$, and wherein said hydroxyapatite particles being present in the glass/hydroxyapatite admixture in an amount of 0.0 wt % to about 50 wt %, such that the first layer has a hydroxyapatite concentration greater than all layers under it, each n intermediate layer under the first layer has a hydroxyapatite concentration greater than the n intermediate layer under it, so there is a gradient of glass/hydroxyapatite admixtures in the multilayered article such that the highest concentration of hydroxyapatite is found in the first layer and the least is found in the n intermediate layer next to the substrate.

These coatings were fired in air or nitrogen. The firings in air were performed in a Unitek dental furnace. The specimens were introduced in the furnace that was preheated to 600° C. Afterward, they were heated at 40° C./min to the desired temperature (between 700 and 860° C.). During heating, the furnace was evacuated to 0.1 atm. Once the maximum temperature was reached, air was let into the chamber and the specimens were fired under 1 atm of air total pressure. After the required time, they were quenched in air. The firings in nitrogen were done in a platinum tubular furnace under nitrogen flow [$p(N_2) \approx 1$ atm, $1 \times 10^{-5}$ m$^3$/s flow]. The specimens were heated at 40° C./min to a temperature between 650 and 850° C. After a programmed period of time, the power of the furnace was shut off. Under these firing conditions of time and temperature, no appreciable grain growth occurred on the alloy. Johnson et al. reported that after 3000 s at 850° C., the average grain diameter of Ti6Al4V plates grew from 2 to 2.1, Johnson et al., *Static grain growth in microduplex Ti6Al4V alloy*, Acta. Mater. 1998, 47:23-29. For the same reason, no degradation in the fatigue strength was expected; also, the firing temperatures were close to the annealing temperatures recommended for Ti6Al4V, Kirkpatrick C. W., Editor, Metals Handbook, Volume 4, 9th ed. Metals Park, Ohio: American Society for Metals; 1981, p 763-774.

The crystallization of the bulk glass and the coatings was evaluated by X-ray diffraction (XRD). The surfaces of the coatings, as well as polished cross sections, were examined by optical microscopy and scanning electron microscopy with associated energy dispersive spectroscopy analysis (SEM-EDS). To study the interfacial reactivity, selected coatings were delaminated by applying pressure or, in the cases with excellent bonding, partially removed by controlled etching with HF. The resulting surfaces were analyzed by SEM-EDS and XRD.

In order to study the adherence of the coatings, the relative crack resistance was qualitatively evaluated by indentation. Vickers indentations on the coating surfaces were performed in air with loads of up to 6.2 kg. Indentations on the coatings and glass-metal interfaces were also performed on polished cross sections using loads ranging from 0.05 to 1.2 kg.

The behavior of selected glass coatings in simulated body fluid (SBF) was studied by in-vitro tests. The specimens (15×10×1 mm) were soaked in SBF at a constant temperature of 36.5° C. for up to 30 days. After soaking, the coatings were rinsed in distilled water, dried, and analyzed by XRD and SEM-EDS.

Table II shows the thermal properties of the fabricated glasses.

TABLE II

Thermal Properties of Metals and Glasses

| | $\alpha^*$ ($10^{-6}$ °C.$^{-1}$) | $T_g$ (° C.) | $T_s$ (° C.) |
|---|---|---|---|
| Ti | ~9.6[1] | | |
| Ti$_6$Al$_4$V | 9.1–9.8[1] | | |
| Bioglass ® | 15.1 | 511 | 557 |
| 6P44-a | 15.6 | 449 | 503 |
| 6P44-b | 13.0 | 516 | 560 |
| 6P44-c | 11.3 | 527 | 599 |
| 6P50 | 12.2 | 522 | 560 |
| 6P53-a | 12.9 | 530 | 565 |
| 6P53-b | 11.5 | 531 | 608 |
| 6P55 | 11.0 | 548 | 602 |
| 6P57 | 10.8 | 557 | 609 |
| 6P61 | 10.2 | 564 | 624 |
| 6P68 | 8.8 | 565 | 644 |

$T_g$, transformation temperature; $T_s$, softening temperature. *Measured between 200 and 400° C.

As expected, an increase in SiO$_2$, and MgO contents reduced α and increased $T_g$ and $T_s$. The softening temperature of all glasses is well below the α→β transformation for Ti6Al4V (955-1010° C.). XRD analysis of the synthesized glasses did no show any crystalline phase with the exception of 6P68 in which sodium calcium phosphate (2.4CaO.0.6Na$_2$O.P$_2$O$_5$) crystals were found. Attempts to fabricate coatings with the original Bioglass® composition always failed because it crystallizes almost completely, even at the lowest firing temperature (700° C.), resulting in poor densification and lack of adhesion to the metal. The main crystalline phase is sodium calcium silicate (Na$_2$Ca$_2$Si$_3$O$_9$). XRD and SEM did not detect significant differences in the crystallization during firing in air or N$_2$.

Figure 3:
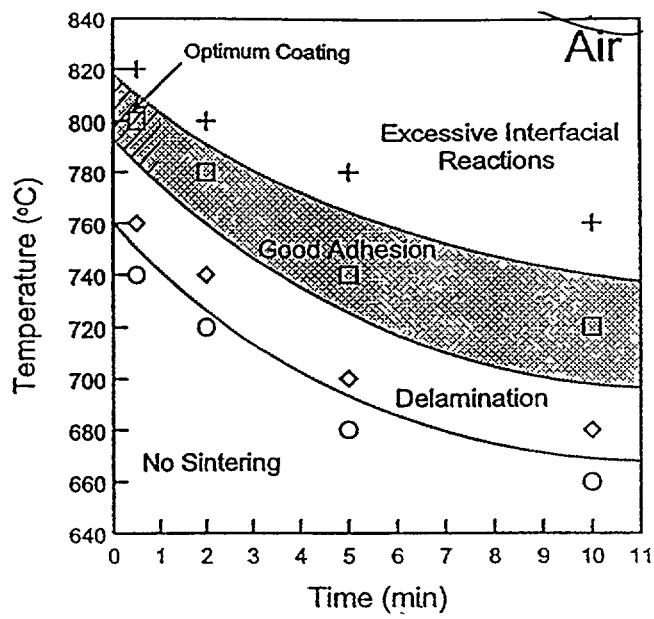
FIG. 3 demonstrates the influence of firing time and temperature on the adhesion of coatings manufactured with glass 6P57, firing done in air, (O) no sintering, (◇) delamination, (□) good adhesion, and (+) excessive interfacial reactions.

It was not possible to prepare 50 μm coatings of glasses 6P55 or 6P53 directly on the metal; however it was possible to prepare coatings containing these glasses when an intermediate glass layer was placed between them and the substrate. Thus, bilayered coatings 6P61/6P55 and 6P57/6P53 could be fabricated. FIG. 3 shows an example of a three layered structure where there is a concentration gradient of HA particles. Table III illustrates some non-limiting examples of multilayered structures prepared in contemplation of the instant invention. "Sub" refers to substrate.

TABLE III

Multilayered glass coatings

| Glass layers | Thickness (μm) | Firing Temp (° C.) | Coating results |
|---|---|---|---|
| Sub/6P68/6P55 | 30/20 | 840 | Cracked |
| Sub/6P61/6P55 | 30/20 | 820 | Good |
| Sub/6P57/6P53 | 30/20 | 800 | Good |
| Sub/6P57/6P50 | 30/20 | 800 | Cracked |
| Sub/6P57/6P53/6P50 | 30/10/10 | 800 | Cracked |
| Sub/6P57/(6P57 + HA)* | 30/20* | 800 | Good |

*HA:6P57 = 50 wt %

Figure 4:
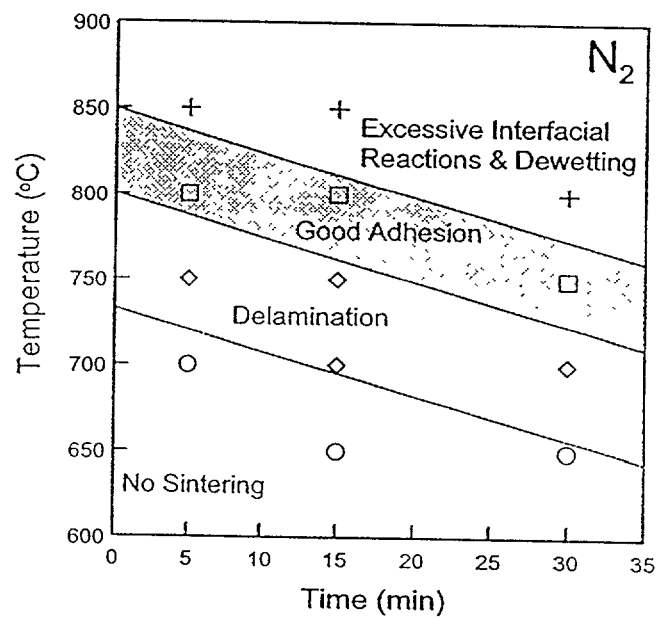
FIG. 4 demonstrates the influence of firing time and temperature on the adhesion of coatings manufactured with glass 6P57, firing done in $N_2$, (O) no sintering, (◇) delamination, (□) good adhesion, and (+) excessive interfacial reactions.
Figure 5:
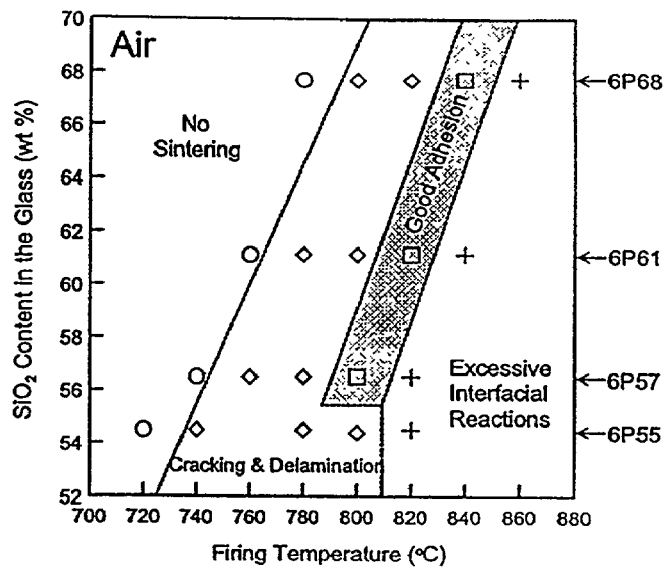
FIG. 5 demonstrates the effect of glass composition and firing temperature in coatings fired in air for 30 s, (O) no sintering, (◇) delamination, (□) good adhesion, and (+) excessive interfacial reactions.
Figure 6:
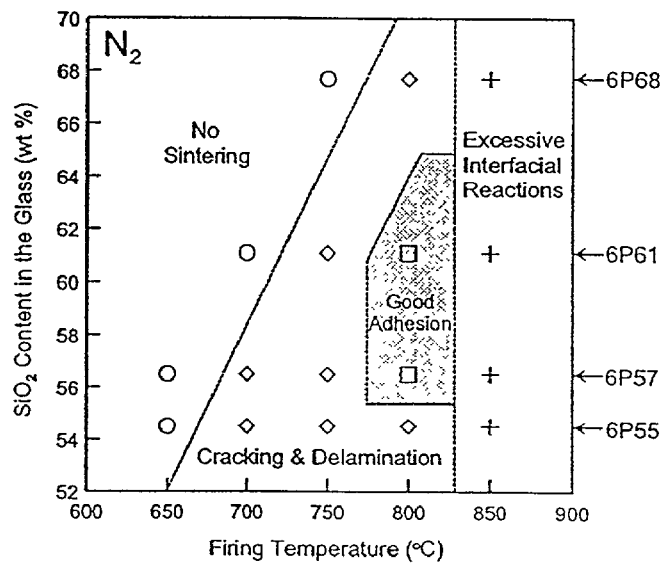
FIG. 6 demonstrates the effect of glass composition and firing temperature in coatings fired in $N_2$ for 30 s, (O) no sintering, (◇) delamination, (□) good adhesion, and (+) excessive interfacial reactions.

The effect of firing time and temperature on the coatings manufactured with glass 6P57 was studied, and the results are shown in FIGS. 3 and 4. Below a critical time and temperature, the glass does not sinter. Then, at higher temperatures, the glass flows and forms a dense layer. Some of these coatings undergo delamination when a 6.2-kg Vickers indentation is applied on the top surface. Nevertheless, a time and temperature region exists where the coatings are dense, exhibit good adhesion, and do not delaminate under indentation tests. In indentations performed at the glass-metal interface on polished cross sections of these coatings, cracks do not propagate along the interface, but rather tend to be driven into the glass. At higher time and temperature, an excessive reaction between the glass and the metal generates gas bubbles at the interface, which results in porous coatings and poor adhesion to the substrate. Depending on the atmosphere, there are some differences in the time and temperature range of each region. Longer firings can be used in $N_2$ than in air to fabricate coatings with optimum adhesion. For example, it is possible to fabricate coatings with good adhesion to the substrate by firing at 800° C. for 15 min in $N_2$ whereas in air an excessive interfacial reaction occurs at this temperature when firings are over 1 min. Another remarkable difference is that some coatings heated in $N_2$ atmosphere undergo dewetting (i.e., the coating recedes to form droplets on the substrate). Thus, in this atmosphere, because of defects present in the coating, dewetting after heating at 800° C. for 30 min damages the final coating. In both atmospheres, a region at the edge of the samples with different coloration and weaker adhesion (it delaminates during indentation) can be observed after long firing times. This region is ~2 mm wide after 10 min at 720° C. in air or 30 min at 750° C. in $N_2$. Coatings fired at 800° C. for times lower than 1 min in air or 15 min in $N_2$ exhibit a homogenous interface with good adhesion to the metal. Based on the previous results, firing times of 30 seconds in air and 15 min in $N_2$ were chosen to study the effect of the glass composition and firing temperature on the coating characteristics. The results obtained by firing in air for these standard conditions were plotted as a function of the Si content in the glasses, FIGS. 5 and 6. The same regions identified in FIGS. 3 and 4 increase in temperature with increasing silica content in the glass. It was possible to fabricate transparent dense coatings with thicknesses ranging from 25 to 150 µm and excellent adhesion to the metal when 6P57 and 6P61 were fired in air at 800 and 820° C., respectively, or at 800° C. in $N_2$.

SEM-EDS examination of the fracture surface in coatings that undergo delamination shows the presence of an interfacial oxide or nitride layer thinner than 0.5 µm for samples fired in air or nitrogen, respectively.

The addition of small amounts of $TiO_2$, approximately 3 wt % broadened the firing range (temperature and time) needed for proper bonding.

The effect of firing temperature on the crystallization of 6P57 and 6P68 coatings was studied. The crystallization of the 6P55 coatings is very similar to that of 6P57. Glasses 6P55 and 6P57 remain practically amorphous up to 780° C., while some sodium calcium phosphate and silicate ($2.4CaO.0.6Na_2O.P_2O_5$ and $Na_2O.3CaO.2SiO_2$) appear at 800° C. At 840° C., diopside crystals [$CaMg(SiO_3)_2$] also grow. The influence of the temperature in the crystallization of 6P61 and 6P68 differs from that for 6P55 and 6P57. Sodium calcium phosphate is the only crystalline phase in 6P61 coatings, and diopside does not crystallize in the coatings of 6P61 and 6P68, even at temperatures as high as 860° C. In the 6P68 coatings silica crystallizes. Tridymite and/or quartz were detected in coatings fired at temperatures over 820° C. The atmosphere (air or $N_2$) does not appreciably affect crystallization. The microstructural studies shown that, for all glasses, the amount of crystals in the coatings with optimum adhesion is below 5 vol %. Consequently, in these cases, crystallization is not expected to substantially affect the thermal expansion of the layers.

In order to identify the reaction phases at the metal-glass interface, coatings of glass 6P57 were removed and the metal surfaces were analyzed by XRD. The coatings fabricated at 740 and 780° C. delaminated easily under pressure. The coating fired at 860° C. fractured readily; bubbles generated by interfacial reactions made it very porous, although fragments of glass remained attached to the metal surface. In samples fired for 3 min at 860° C., most of the glass separated.

Figure 7:
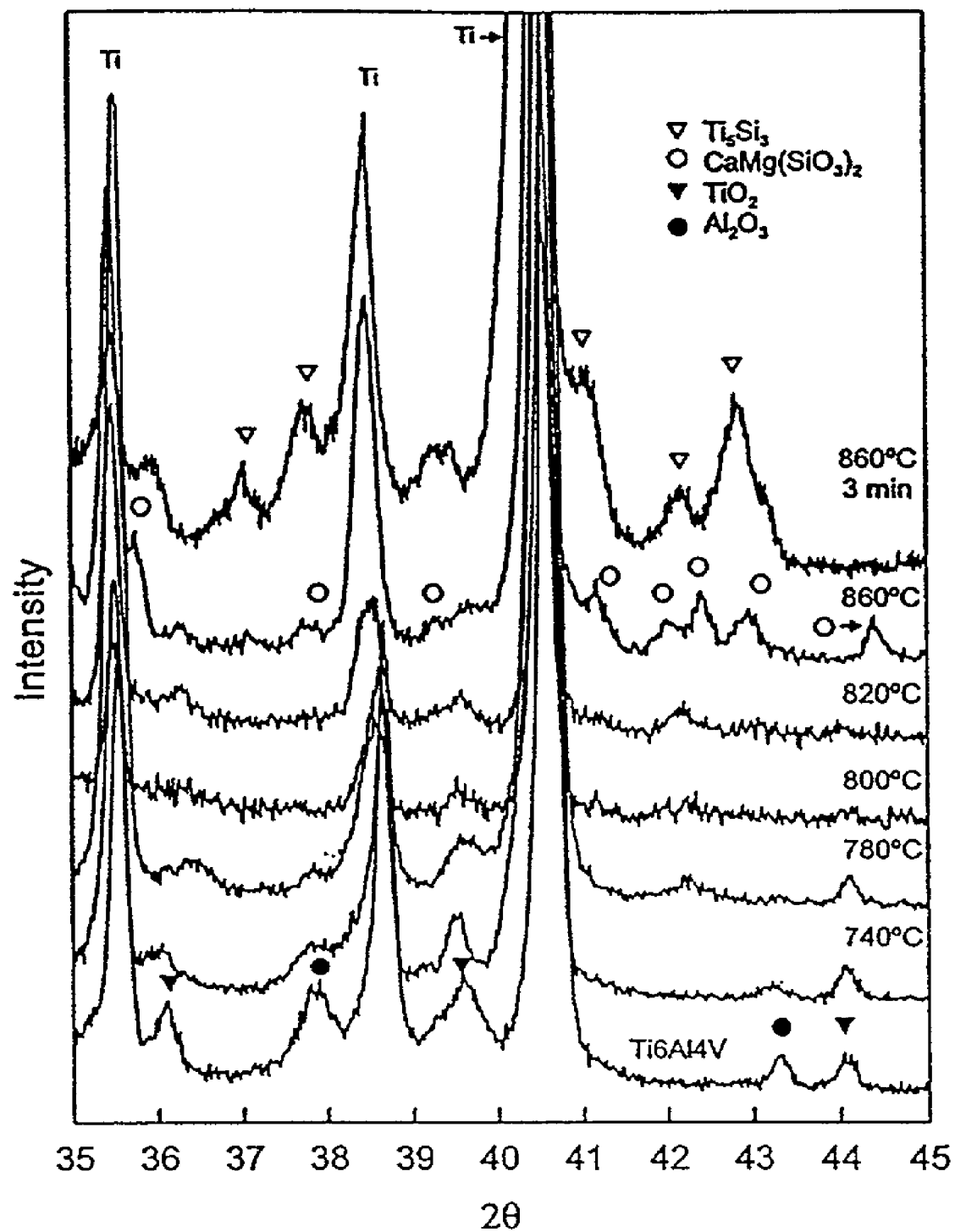
FIG. 7 shows an XRD pattern for Ti6Al4V substrates before and after removing 6P57 coatings fired for 30 s in the temperature range of 740-860° C. and for 3 min at 860° C.

Coatings fired at 800 and 820° C. did not delaminate; therefore the glass layer was etched with HF until some isolated spots of metal appeared. The XRD patterns of Ti6Al4V plates after removing coatings fired at different temperatures are shown in FIG. 7. The starting metal surface is covered by a thin layer of oxides (because Ti6Al4V readily oxidizes). Only peaks from Ti, $TiO_2$ and $Al_2O_3$ can be detected in the plates fired at temperatures lower than 800° C. The oxide peaks disappear after firing at temperatures between 800 and 820° C. (where good adhesion occurs. The glass that remains attached to the metal surface after scraping the coating fired at 860° C. contains diopside. A titanium silicide, $Ti_5Si_3$, can be also detected in this specimen, although its peaks overlap with those from the diopside.

The Ti6Al$_4$V-6P57 interface generated by firing at 840° C. for 30 s was studied by SEM-EDS. Most of the coating was removed from the metal. Diopside crystals were seen on the glass that remained attached. The surface of the substrate had a granular texture. According to the EDS analysis, silicon and phosphorus were found on the substrate surface but not the other components of the glass. The presence of Si agreed with the observation by XRD of a titanium silicide layer.

Figure 2:
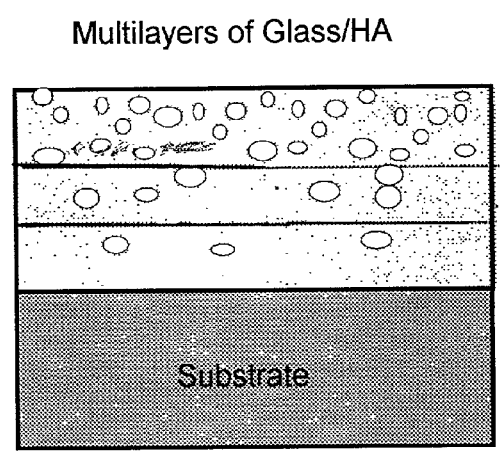
FIG. 2 demonstrates a multilayered structure where the HA particles are in a present in a gradient concentration where the density of HA is greater towards the outer layers.
Figure 8:
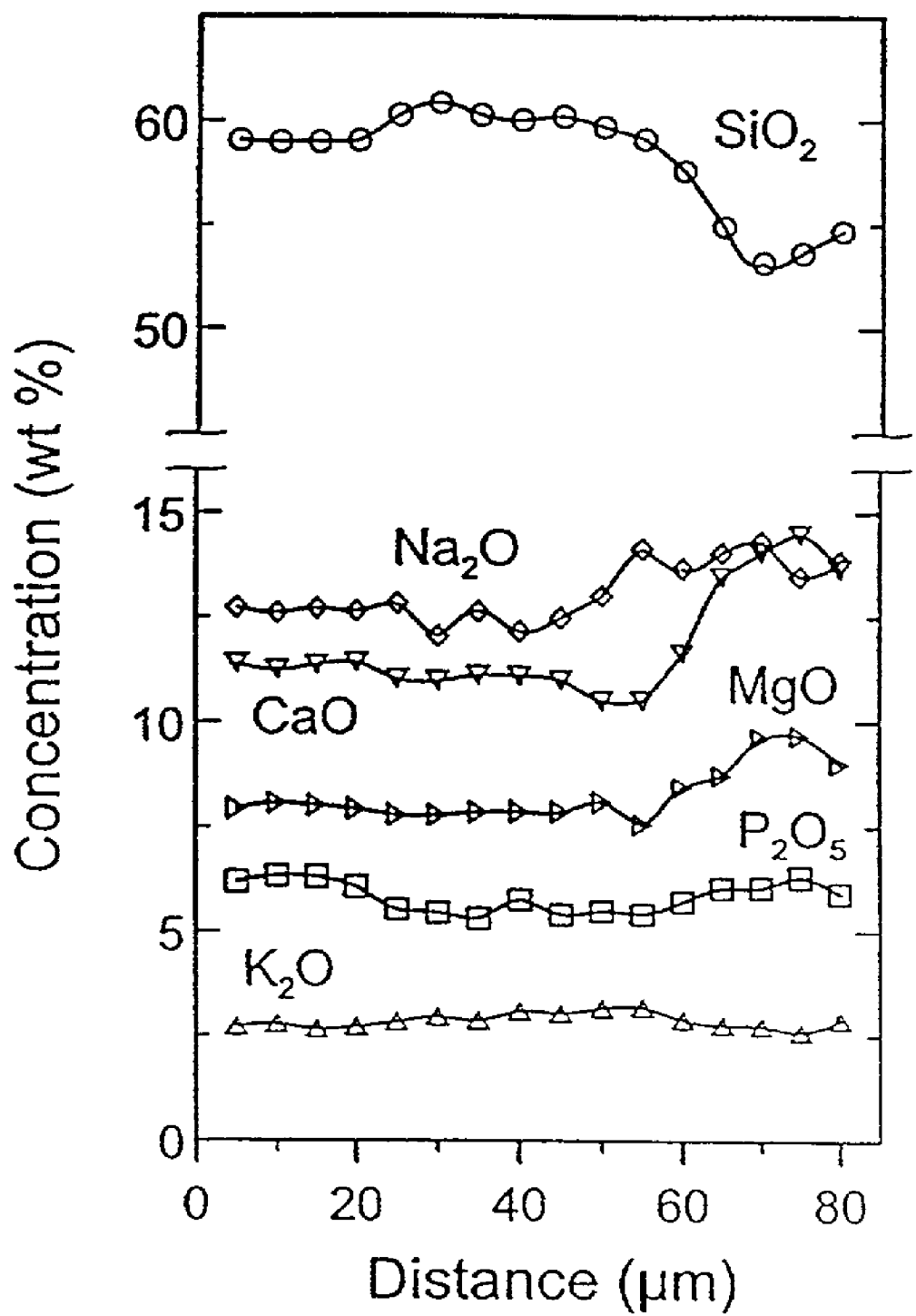
FIG. 8 shows the elemental line analysis (calibrated EDS) along the cross sections of a bilayer 6P61/6P55 coating. Distance along the x-axis refers to the distance from the substrate.

Multilayered coatings were fabricated by the sequential deposition method, FIG. 2. The instant invention is not limited to any particular deposition process. It is contemplated that any deposition process is suitable for the making the article of the instant invention. The selected firing temperature for the multilayered coating was the optimum for the glass in contact with the substrate. In one preferred embodiment a gradient in composition, and therefore in thermal expansion, was achieved, that could help increase the mechanical stability of coatings whose external layer will have a lower $SiO_2$ content. Although a coating of 6P55 placed directly on Ti6Al4V cracked during cooling, when an intermediate 6P61 layer was placed between the 6P55 and the alloy, the coatings did not crack after cooling or delaminate during indentation tests. Moreover, a smoother gradient could also be obtained by locating a layer of glass 6P57 between the 6P61 and 6P55. The SEM-EDS line analysis along the cross sections of the metal coated with 6P61/6P55 (70:30 thickness ratio, 75-µm overall thickness) is shown in FIG. 8. A drop in the Si concentration can be clearly detected because 6P61 is 6 wt % richer in silica than 6P55 (Table 1). Besides, the analysis of Ca, Na, and Mg reveals a slight increase in their concentration at the same height of the coating, which is in agreement with their increasing concentrations in the glasses. In general, it was possible to fabricate coatings with an outer layer having a silica content as low as 53 wt % that did not delaminate during cooling or indentation. Layers with less silica content cracked during cooling.

To enhance the bioactivity, layered coatings with a mixture of glass and HA particles in the external layer were also fabricated. A coating was prepared where the first layer is formed by glass 6P57 and the second is a mixture of synthetic HA particles (<20 µm) and glass 6P57 (50:50 wt % ratio). The thickness ratio between the internal and external layer was ~70:30. This coating was fired in air at 800° C. for 30 s and showed excellent adhesion; it did not crack during cooling or delaminate during indentation tests.

The analysis of the samples immersed in SBF for 30 days showed the presence of HA crystals precipitating on layers with silica content lower than or equal to 57 wt %. HA also grew on the surface of the multilayer coatings containing HA particles.

While not wishing to be bound by any particular theory, the following sequence of steps can be proposed for coatings fired in air. During heating, gas flows easily through the porous deposited coating and forms an oxide layer on the alloy surface. When the glass softens and flows, it starts to dissolve the oxides and, once they have been completely dissolved, redox reactions can occur at the glass-metal interface. According to the interfacial analysis, the main reaction is the formation of $Ti_5Si_3$.

In the coatings with optimum adhesion (i.e., those that did not delaminate during indentation), it was not always possible to detect any interfacial layer with the analytical tools used in this work. Some TEM evidence reveals a $Ti_5Si_3$ interfacial layer approximately 150 nm thick in coatings with optimum adhesion. Nevertheless, the diffusion of oxygen can affect the quality of the interface at the periphery of the samples. At the edge of the coatings where the diffusion distances are shorter, oxygen from the atmosphere can reach the interface and oxidize the alloy surface. The oxide scales are porous so the air can easily flow through, forming an interfacial oxide layer that grows inward. This oxide can be detected by XRD in the samples fired for longer and results in a peripheral region with poor adhesion to the metal. Optimum coatings are obtained when the firing period is very short (<1 min), so the growth of this oxide layer is negligible, resulting in homogenous interfaces.

While not wishing to be bound by any particular theory, a similar sequence of stages can be proposed for the firings achieved in $N_2$. In this case, the nitride layer formed during heating disappears by reacting with silica in the coating, according to Reaction (1).

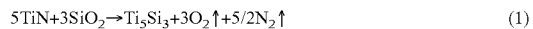

$$5TiN + 3SiO_2 \rightarrow Ti_5Si_3 + 3O_2\uparrow + 5/2N_2\uparrow \qquad (1)$$

Once the nitride layer formed during heating disappears, the redox reactions can take place at the glass-metal interface. Reaction (1) seems to be slower than the dissolution of titanium oxide, and longer firing times can be used in nitrogen to obtain good adhesion. As with the air firings, if a nitride layer remains in the interface after firing, the coatings delaminate during the indentation tests. An interfacial layer was not always detected in the samples with the optimum adhesion, although an interfacial nitride layer growing inward from the edge of the coatings could be observed in the samples fired for longer times. Some TEM evidence reveals a $Ti_5Si_3$ interfacial layer approximately 150 nm thick in coatings with optimum adhesion. The contact angle of the glass on the nitride layer seems to be high, and the growth of the nitride layer is accompanied by dewetting of the coating (i.e. the glass recedes on the substrate). This adds a new factor when considering firings in nitrogen, because longer times are usually needed. For example, complete dewetting was observed on samples fired at 800° C. for 30 min. Even in those samples fired for shorter times, dewetting can occur, starting at defects originated during the deposition of the glass powder. Obtaining good results in nitrogen firings requires controlling the quality of the deposited layers to avoid defects that can grow because of the receding of the glass.

Dissolution of the oxide layer in the glass during firing in air would provide the required interfacial saturation. Then the optimum firing conditions correspond to the moment in which $TiO_x$ is completely dissolved and the interface is saturated. However this fails to explain the fabrication of coatings with good adhesion in $N_2$ where no $TiO_x$ seems to form. While not wishing to be bound by any particular theory, another explanation is that the role of the oxide or nitride layer is to provide a temporary buffer between the glass and the metal, which allows the glass to flow and density without redox interfacial reactions.

From the previous discussion it can be seen that the adequate fabrication temperature for each coating is related to the temperature at which the glass softens and flows. The higher the softening point, the higher the temperature for the glass to flow. Consequently, the temperature limits of the different regions described in FIGS. 5 and 6 (lack of sintering, delamination, good adhesion, and excessive interfacial reactions) are proportional to the silica content of the glass. For example, 6P68 coatings should be fired for 30 s at 840° C. in order to achieve the optimum adhesion; for the same firing time, 6P57 should be fired at 800° C.

The coatings crystallize more than a bulk piece of the same glass because of the concentration of impurities on the surface of the powder particles. The glass composition accounts for the different crystallization behaviors of the glasses. Sodium calcium phosphate crystallizes in all the studied glasses; but the reduction in calcium and magnesium content from 6P57 to 6P61 inhibits the crystallization of diopside, and the high silica content of glass 6P68 results in the crystallization of $SiO_2$ (Table 1). The 6P68 coatings fail after firing in $N_2$ because they crystallize extensively after times longer than 5 min at 850° C., which renders a brittle glass-ceramic layer.

Although the thermal expansion of glass 6P55 is very similar to that of 6P57 (11.0 vs. 10.8), all the coatings fabricated with glass 6P55 (or glasses with lower silica content) crack and/or delaminate even for thickness as low as 25 μm. Finally, it should be taken into account that thin coatings (25 μm) usually have more defects as a consequence of the deposition technique.

In the multi-layered approach contemplated by the instant invention, some inter-diffusion between the layers can help to ease thermal stresses, and a reduction in the edge stresses is also expected. From the processing viewpoint, the better wetting of glass on glass makes it easier to fabricate thin layers (down to 10 μm) without the defects observed in the thinner monolayer films. One advantage of the multilayer approach is that it permits the fabrication of coatings with silica contents as low as 53 wt % in the external layer or to incorporate HA particles maintaining excellent adhesion to the metal. Some of these coatings form HA during in vitro tests. Future optimization of the coating design could include bioactive outside layers over insoluble glasses with good adhesion to the substrate.

When using glass-HA mixtures, two kinds of stresses coming from differences in thermal expansion coefficients must be considered (i) between glass and HA (reported $\alpha_{HA}$ ranges between $11.6-14.0 \times 10^{-6\circ}$ $C.^{-1}$) and (ii) between the glass-HA composite and the metallic substrate. Using the Turner model (with similar Poisson's ratio for HA and glass, Kingery et al. Introduction to Ceramics, $2^{nd}$ (John Wiley & Sons, New York, 1976), p. 604.), the overall thermal expansion of the composite (6P57-HA 50 wt %) will range between $\alpha=11.2-12.2\times10^{-6\circ}$ $C.^{-1}$, ($d_{6P57}=2.60$ g/cm$^3$, $d_{HA}=3.15$ g/cm$^3$). No cracks could be detected either at the glass/HA or glass/metal interfaces, so the coating can endure the tension created by the HA particles embedded in the outer surface.

The HA particles enhanced the capacity of the coatings to precipitate apatite when immersed in SBF.

It will be appreciated by those skilled in the art that various modifications and extrapolations can be made in the process and article as described herein without departing from the spirit and scope of the invention. All references cited above are hereby incorporated by reference in their entirety into the instant specification.

We claim:

1. A multilayer article comprising,
a metal substrate,
a first layer comprising an inner and outer surface,
said first layer comprising a glass composition,
a first intermediate layer having an inner and outer surface, and said first intermediate layer is located between the substrate and the first layer, said first intermediate layer comprises a glass composition,
wherein each said glass composition comprises,
44.2 to 67.7 wt % SiO2, 10.1 to 23.4 wt % CaO, 5.7 to 13.3 wt % MgO, 10.3 to 23.6 wt % $Na_2O$, 2.2 to 6.5 wt % $K_2O$ and 6.0 wt % $P_2O_5$,
and contains hydroxyapatite particles in an amount of up to 50 wt %.

2. The multilayer article of claim 1,
wherein there is a second intermediate layer located between the first intermediate layer and the substrate,
said first layer, first intermediate layer and said second intermediate layer all comprising a glass composition as defined in claim 1,
wherein the hydroxyapatite concentration is highest in the first layer, lowest in the second intermediate layer, and present in the first intermediate layer in an amount that is in between the first layer and the second intermediate layer.

3. The multilayer article of claim 2,
wherein the glass composition in the first layer, the first intermediate layer and the second intermediate layer each comprise about 61.1 wt % $SiO_2$, about 12.6 wt % CaO, about 7.2 wt % MgO, about 10.3 wt % $Na_2O$, about 2.8 wt % $K_2O$ and about 6.0 wt % $P_2O_5$ and the hydroxyapatite amount in the first layer comprises 50 wt %
and the substrate is Ti or $Ti_6Al_4V$.

4. The multilayer article of claim 1,
wherein the substrate is Ti or $Ti_6Al_4V$.

5. The multilayer article of claim 1,
wherein the glass composition in the first layer comprises about 54.5 wt % $SiO_2$, about 15 wt % CaO, about 8.5 wt % MgO, about 12.0 wt % $Na_2O$, about 4.0 wt % $K_2O$ and about 6.0 wt % $P_2O_5$,
and the glass composition in the first intermediate layer comprises
about 61.1 wt % $SiO_2$, about 12.6 wt % CaO, about 7.2 wt % MgO, about 10.3 wt % $Na_2O$, about 2.8 wt % $K_2O$ and about 6.0 wt % $P_2O_5$,
and the substrate is Ti or $Ti_6Al_4V$.

6. The multilayer article of claim 1,
wherein the glass composition in the first layer comprises about 52.7 wt % $SiO_2$, about 12.6 wt % CaO, about 7.1 wt % MgO, about 17.0 wt % $Na_2O$, about 4.6 wt % $K_2O$ and about 6.0 wt % $P_2O_5$,
and the glass composition in the first intermediate layer comprises:
about 56.5 wt % $SiO_2$, about 15 wt % CaO, about 8.5 wt % MgO, about 11.0 wt % $Na_2O$, about 3.0 wt % $K_2O$ and about 6.0 wt % $P_2O_5$,
and the substrate is Ti or $Ti_6Al_4V$.

7. The multilayer article of claim 1,
wherein the glass composition in the first layer and the first intermediate layer comprise about 56.5 wt % $SiO_2$, about 15 wt % CaO, about 8.5 wt % MgO, about 11.0 wt % $Na_2O$, about 3.0 wt % $K_2O$ and about 6.0 wt % $P_2O_5$ and the hydroxyapatite amount in the first layer is 50 wt %,
and the substrate is Ti or $Ti_6Al_4V$.

8. The multilayer article of claim 1, wherein:
the first layer has a glass composition which has a $SiO_2$ content between about 53 to about 57 wt %.

9. The multilayer article of claim 8, wherein:
n=2.

10. The multilayer article of claim 1, wherein:
the first layer has a glass composition which has a $SiO_2$ content between about 56 to about 67.7 wt %.

11. The multilayer article of claim 10, wherein:
n=2.

12. The multilayer article of claim 1,
wherein there is a second intermediate layer located between the first intermediate layer and the substrate,
said first layer, first intermediate layer and said second intermediate layer all comprising a glass composition as defined in claim 1,
wherein the $SiO_2$ concentration is lowest in the first layer, highest in the second intermediate layer, and present in the first intermediate layer in an amount that is in between the first layer and the second intermediate layer.

13. A multilayer article comprising,
a metal substrate comprising Ti or $Ti_6Al_4V$,
n intermediate layers, where n is an integer,
a first layer comprising an inner and outer surface,
said n intermediate layers disposed between the metal substrate and the first layer,
wherein the n intermediate layers and the first layer each independently comprise a glass/hydroxyapatite admixture comprising a glass composition and hydroxyapatite particles (HA),
said glass composition comprising,
about 44.2 to about 67.7 wt % $SiO_2$, about 10.1 to about 23.4 wt % CaO, about 5.7 to about 13.3 wt % MgO, about 10.3 to about 23.6 wt % $Na_2O$, about 2.2 to about 6.5 wt % $K_2O$ and about 6.0 wt % $P_2O_5$,
and wherein said hydroxyapatite particles being present in the glass/hydroxyapatite admixture in an amount of up to 50 wt %.

14. The multilayer article of claim 13, wherein:
the first layer has a glass composition which has a $SiO_2$ content between about 53 to about 57 wt %.

15. The multilayer article of claim 14, wherein:
n=2.

16. The multilayer article of claim 13, wherein:
the first layer has a glass composition which has a $SiO_2$ content between about 56 to about 67.7 wt %.

17. The multilayer article of claim 16, wherein:
n=2.

* * * * *